United States Patent [19]

Shamsuddin

[11] Patent Number: 5,082,833
[45] Date of Patent: Jan. 21, 1992

[54] REDUCTION OF CELL PROLIFERATION AND ENHANCEMENT OF NK-CELL ACTIVITY

[76] Inventor: Abulkalam M. Shamsuddin, 2916 Old Court Road, Baltimore, Md. 21208

[21] Appl. No.: 213,889

[22] Filed: Jun. 30, 1988

[51] Int. Cl.$^5$ ............ A61K 31/45; A61U 31/66
[52] U.S. Cl. ................................. 514/143; 514/724
[58] Field of Search ............................ 514/143, 729

[56] References Cited

PUBLICATIONS

R. B. Heberman et al., J. Natl. Cancer Inst. 62 (3), 441–445 (1979).
R. B. Heberman et al., Science 214, 24–30 (1981).
Dyer, An Index of Tumor Chemotherapy, Wilt, 8/13/51, pp. 10–12, 151 and 152.
Elsayeo et al., Lab Invest, vol. 56, No. 1, 1987, p. 21 A.

*Primary Examiner*—Stanley J. Friedman
*Attorney, Agent, or Firm*—Millen, White & Zelano

[57] ABSTRACT

A method for moderating the rate of cellular mitosis in a living mammalian tissue having a pathologically elevated rate of cellular mitosis sensitive to treatment with a solution below which comprises perfusing said tissue under mitotic growth conditions with a safe and effective amount and concentration of a composition consisting essentially of a) inositol hexaphosphate or a physiologically acceptable salt thereof; and b) a source of inositol or a physiologically acceptable salt thereof, for a period of time sufficient to moderate the elevated rate of cellular mitosis to a normal, non-pathological rate for said tissue. The method is useful in human and mammalian diseases wherein NK cell activity is altered in the laboratory, e.g. tumors, other cancers including leukemia, immunosuppressed individuals (AIDS and transplant recipients), and in viral, fungal or protozoal infections.

20 Claims, 4 Drawing Sheets

REDUCTION OF CELL PROLIFERATION AND ENHANCEMENT OF NK-CELL ACTIVITY

DESCRIPTION OF THE INVENTION

1. Technical Field of the Invention

This invention relates to compositions comprising a mixture of inositol (I) and inositol hexaphosphate ($IP_6$) and their use in normalizing the rate of mitosis sensitive to treatment with a solution below in mammalian tissues wherein said rate is abnormally high, e.g. in various cancers. This invention also relates to the use of such compositions in enhancing reduced natural killer cell (NK-cell) activity, e.g. in patients whose immune systems are abnormally suppressed due to disease (e.g., AIDS), chemotherapy, preparation for transplant reception, etc.

2. Background Art

Inositol (hexahydroxycyclohexane) and its phosphates are well known, nontoxic, naturally occurring compounds which have been used for a number of pharmaceutical applications. Inositol is a 6-carbon sugar that is present in both animal and plant cells, either as a part of a larger molecule, e.g. phospholipids, or in phosphorylated form, e.g. the various inositol phosphates. Inositol triphosphate ($IP_3$) is known to be important in the regulation of cell proliferation, a key event in cancer formation; some authors have suggested that IP3 causes a release of intracellular calcium, which is an essential rate regulator, bringing about cell division and proliferation; see R. A. Steinhardt & J. Alderton, *Nature* 332: 364–366 (1988).

The inositols can be commercially prepared by a number of methods, e.g. see Posternak U.S. Pat. No. 1,313,014; Goedecke U.S. Pat. No. 1,715,031; Wagner, U.S. Pat. No. 1,716,286; Goedecke U.S. Pat. No. 1,721,214; U.S. Pat. No. 2,112,553; Elkin, U.S. Pat. No. 2,414,365; etc.

Revici, U.S. Pat. No. 3,470,295 describes therapeutic compositions for treating posttraumatic shock, pain and hemorrhage in which one of the compounds thereof is maltose, inositol, or sorbitol. Bodor et al., U.S. Pat. No. 4,154,824 describe the use of the potassium salt of inositol hexaphosphate (phytic acid) in administering potassium to a mammal without imparting a metallic potassium aftertaste. Nicolau et al., U.S. Pat. Nos. 4,192,869; 4,321,259; and 4,473,563, describe inositol hexaphosphate-containing lipid vesicles which are not in solution but rather fused to erythrocytes to provide improved oxygen release properties. More recently, Siren U.S. Pat. No. 4,735,936, the contents of which are incorporated by reference herein, describes the use of inositol triphosphate or its salts in the treatment of conditions caused or aggravated by cadmium or aluminum or free radicals in the body.

Graf et al., in *Cancer* 56: 717–718 (1985) suggested a relationship between diet and colonic cancer in which inflammatory bowel diseases might be suppressed by diets rich in phytic acid, which is believed to be based on the suppression by dietary phytate of iron catalyzed oxidative processes producing hydroxy radicals. Shamsuddin et al., in *Carcinogenesis* 9(4): 577–580 (1988) demonstrated that there are indeed some correlations between dietary factors (specifically the effect of sodium inositol hexaphosphate or "phytate") and the incidence of large intestinal cancer in laboratory rats.

Cancer is, of course, well known as a major health problem in the world today. In spite of vast sums which have been spent in pursuit of remedies, very few drugs have been shown to be effective in either treatment or prevention of cancer, and those which have are for the most part characterized by their high toxicity and relatively poor tolerance.

DISCLOSURE OF THE INVENTION

It is an object of the present invention to provide a method for moderating the rate of cellular mitosis in a living mammal having a pathologically elevated rate of cellular mitosis, sensitive to treatment with the solution below, which comprises administering to the mammal a safe and effective amount of solution of a) inositol hexaphosphate or a physiologically acceptable salt thereof; and b) inositol or a physiologically acceptable salt thereof, in a molar ratio of a):b) from about 1:3 to 3:1 effective to moderate the elevated rate of cellular mitosis to a normal, non-pathological rate.

It is another object of the present invention to provide a method for enhancing the rate of NK cell activity in a living mammal having a pathologically or pharmaceutically decreased rate of tumoricidal activity and reduced NK cell activity, which comprises administering to the mammal an amount of a solution of a) inositol hexaphosphate or a physiologically acceptable salt thereof, and b) inositol or a physiologically acceptable salt thereof, in a molar ratio of a):b) of about 1:3 to 3:1, effective to enhance the rate of NK-cell activity to a normal, non-pathological rate.

A further object of the present invention is to provide such a method and composition for therapeutic use in cases of immunosuppression, e.g., in patients having AIDS or undergoing treatment such as chemotherapy or preparation for transplant reception.

An additional object of the present invention is to provide such a method and composition for therapeutic use in cases of bacterial, viral, fungal, and protozoal infections.

A more particular object of the present invention is to provide a pharmaceutical composition suitable for use in such methods, preferably adapted for enteral or parenteral administration and especially labeled for at least one of the above uses.

Upon study of the specification and appended claims, further objects, features and advantages of the present invention will become more fully apparent to those skilled in the art to which this invention pertains.

BEST MODE FOR CARRYING OUT THE INVENTION

Briefly, the above and other objects, features and advantages of the present invention are attained in one aspect thereof by providing a method for moderating the rate of cellular mitosis in a living mammalian tissue having a pathologically elevated rate of cellular mitosis (e.g., as reflected in abnormally high cell proliferation), which comprises perfusing said tissue under mitotic growth conditions with a safe and effective amount and concentration of a composition consisting essentially of a) inositol hexaphosphate or a physiologically acceptable salt thereof; and b) a source of inositol or a physiologically acceptable salt thereof, for a period of time sufficient to moderate the elevated rate of cellular mitosis to a normal, non-pathological rate for said tissue. By the term "perfusion" as used herein is meant exposing the tissue to a solution of the active compounds, e.g. by flowing blood or any other physiologically acceptable fluid having the compounds dissolved therein across or through the tissue being treated. Generally the molar ratio of a) to b) is about 1:10 to 10:1, preferably about 1:3 to 3:1 and especially about 1:1.

The compounds of this invention can be employed in admixture with conventional excipients, i.e., pharmaceutically acceptable organic or inorganic carrier substances suitable for parenteral, enteral (e.g., oral) or topical application which do not deleteriously react with the pharmacologically active compounds. Suitable pharmaceutically acceptable carriers include but are not limited to water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid monoglycerides and diglycerides, pentaerythritol fatty acid esters, hydroxymethyl cellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds. They can also be combined where desired with other active agents, e.g. vitamins.

For parenteral application, particularly suitable are injectable, sterile solutions, preferably oily or aqueous solutions, as well as suspensions, emulsions, or implants, including suppositories. Ampoules are convenient unit dosages.

For enteral application, particularly suitable are tablets, dragees, liquids, drops, suppositories, or capsules. A syrup, elixir, or the like can be used wherein a sweetened is employed.

Sustained or directed release compositions can be formulated, e.g., liposomes or those wherein the active compound is protected with differentially degradable coatings, e.g. by micro-encapsulation, multiple coatings, etc. It is also possible to freeze-dry the compounds and use the lyophilizates obtained, for example, for the preparation of products for injection.

For topical application, non-sprayable viscous to semisolid or solid non-sprayable forms comprise a carrier compatible with topical application and having a dynamic viscosity preferably greater than water. Suitable formulations include but are not limited to solutions, suspensions, emulsions, creams, ointments, powders, liniments, salves, aerosols, etc. which are, if desired, sterilized or mixed with auxiliary agents, e.g. preservatives, stabilizers, wetting agents, buffers, salts for influencing osmotic pressure, etc. Also suitable for topical application are sprayable aerosol preparations wherein the active ingredient, preferably in combination with a solid or liquid inert carrier material, is packaged in a squeeze bottle or in admixture with a pressurized, volatile, normally gaseous propellant, e.g. a freon.

Oral administration is presently preferred although, depending on the location and nature of the tissue being treated, other known types of administration can be preferred, e.g. intravenous administration for treatment of blood cancers such as leukemia; parenteral administration for direction to other body fluids such as pericardial, spinal, pleural, etc.; use in a rectal enema wash for use in treatment large intestinal cancer, etc.; bladder wash or irrigation, and the like.

Generally, the compounds of this invention are dispensed in unit dosage form comprising about 0.1 to 10 g. in a pharmaceutically acceptable carrier per unit dosage. They are incorporated in topical formulations in concentrations of about 1 to 10 weight percent.

The daily dosage of the compounds according to this invention is generally about 10 to 500 mg/kg/day, preferably 50 to 100 mg/kg/day, when administered to humans to treat large intestinal cancer.

It will be appreciated that the actual preferred amounts of active compound in a specific case will vary according to the specific compound ratios being utilized, the particular compositions formulated, the mode of application, and the particular situs and organism being treated. Dosages for a given host can be determined using conventional considerations, e.g. by comparison of the differential activities of the pharmaceutically active compounds of this invention with known agents by means of an appropriate conventional pharmacological protocol and extrapolation of the dosages based on the results thereof, as is known in the art.

In one aspect of the present invention, the pathological elevated rate of cellular mitosis is caused by cancer, e.g. cancer of the blood, i.e. a leukemia, or large intestinal cancer in which the cellular mitosis is sensitive to treatment with a solution of this invention.

In another aspect of the present invention, the abnormally low rate of NK cell tumoricidal activity is caused by immunosuppression, which can be the result of a disease such as cancer or pharmacologically induced. Examples include but are not limited to Acquired Immune Deficiency Syndrome (AIDS) and immunosuppression which is pharmaceutically induced in preparation for receiving a tissue transplant or by cancer chemotherapy agents commonly used today.

In another aspect of this invention, the immuno suppression is caused by a bacterial, viral, fungal, or protozoal infection. For Example, see R. Herberman and J. Ortaldo in *Science* 214: 24–30 (1981) and J. L. Marx in *Science* 251: 1367–1369 (1986), the contents of which are incorporated by reference herein.

In a compositional aspect, the present invention provides a pharmaceutical composition for moderating the rate of cellular mitosis sensitive to treatment with a solution of this invention in a living mammalian tissue having a pathologically elevated rate of cellular mitosis by perfusing said tissue under mitotic growth conditions, for a period of time sufficient to moderate the elevated rate of cellular mitosis to a normal, non-pathological rate for said tissue, which comprises a safe and effective amount and concentration of composition consisting essentially of a) inositol hexaphosphate or a physiologically acceptable salt thereof; and b) a source of inositol or a physiologically acceptable salt thereof. Generally, the molar ratio of a) to b) is about 1:10 to 10:1, preferably about 1:3 to 3:1 and especially about 1:1.

The pharmaceutical compositions of the present invention can be adapted for intravenous administration as is known in the art, e.g. see *Remington's Pharmaceutical Science*, 15th Edition (1975), especially Part 8: Pharmaceutical Preparations and Their Manufacture, the contents of which are incorporated by reference herein. The compositions are preferably packaged in unit dosage form, e.g. 0.1–10 g. of active ingredient per unit dosage which can be given one or more times per day. Preferably, the composition is packaged in a sterile container and labeled for use according to the process of this invention.

While not wishing to be bound by any theory of the invention, it is presently believed that a mixture of the molecules of inositol and inositol hexaphosphate may give rise to various inositol phosphates (from the monophosphates to the pentaphosphates) in addition to the starting materials which are administered. In most biological systems, an excess of rate limiting substance enhances the rate of the reaction. Thus, one effect of the present composition on cells (whether normal or cancerous) would have been expected to be an increase in IP3, which would result in even more cell proliferation. Paradoxically, this has not been observed and instead the mixture of inositol and inositol hexaphosphate has been shown not only to prevent cancers, but also to be effective in treatment. Furthermore, as there has been minimal or no detectable toxic effects observed in standard screening rodents, and in view of inositol's wide occurrence in nature, it would appear from such data to probably be safe for human use.

More specifically, the NK cell activity is known to be altered in tumors, in immunuosuppressed individuals, and in bacterial, viral, fungal and protozoal infections. Not only does the composition of the present invention enhance NK cell activity when fed to mice in vivo, it also enhances the NK cell activity when NK cells are treated in vitro, even for a short period of time; the mixture of the present invention is more effective than either of its individual ingredients used alone. Because of its clearly demonstrated in vitro activity against a human leukemia cell line, NK cells and tumor cells, administration to patients with immunodeficiency syndromes and cancers seems clearly indicated.

BRIEF DESCRIPTION OF THE DRAWINGS

Referring to the annexed drawings, like or corresponding reference characters refer to like or corresponding parts in the several figures, wherein.

DETAILED DESCRIPTION

Figure 1:
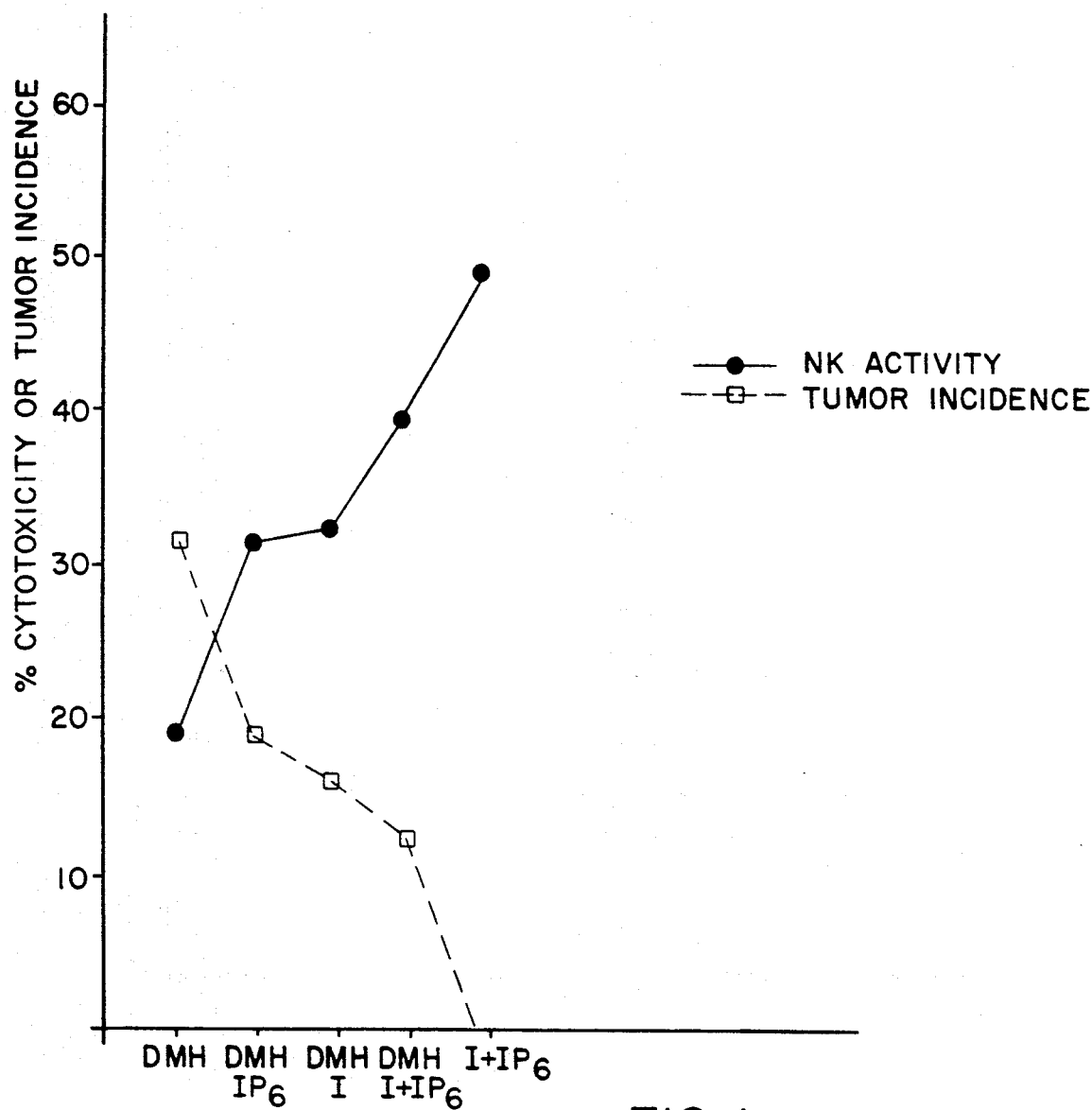
FIG. 1 shows the inverse relationship of NK-cell activity and tumor incidence following in vivo administration of the composition of the present invention.
Figure 2:
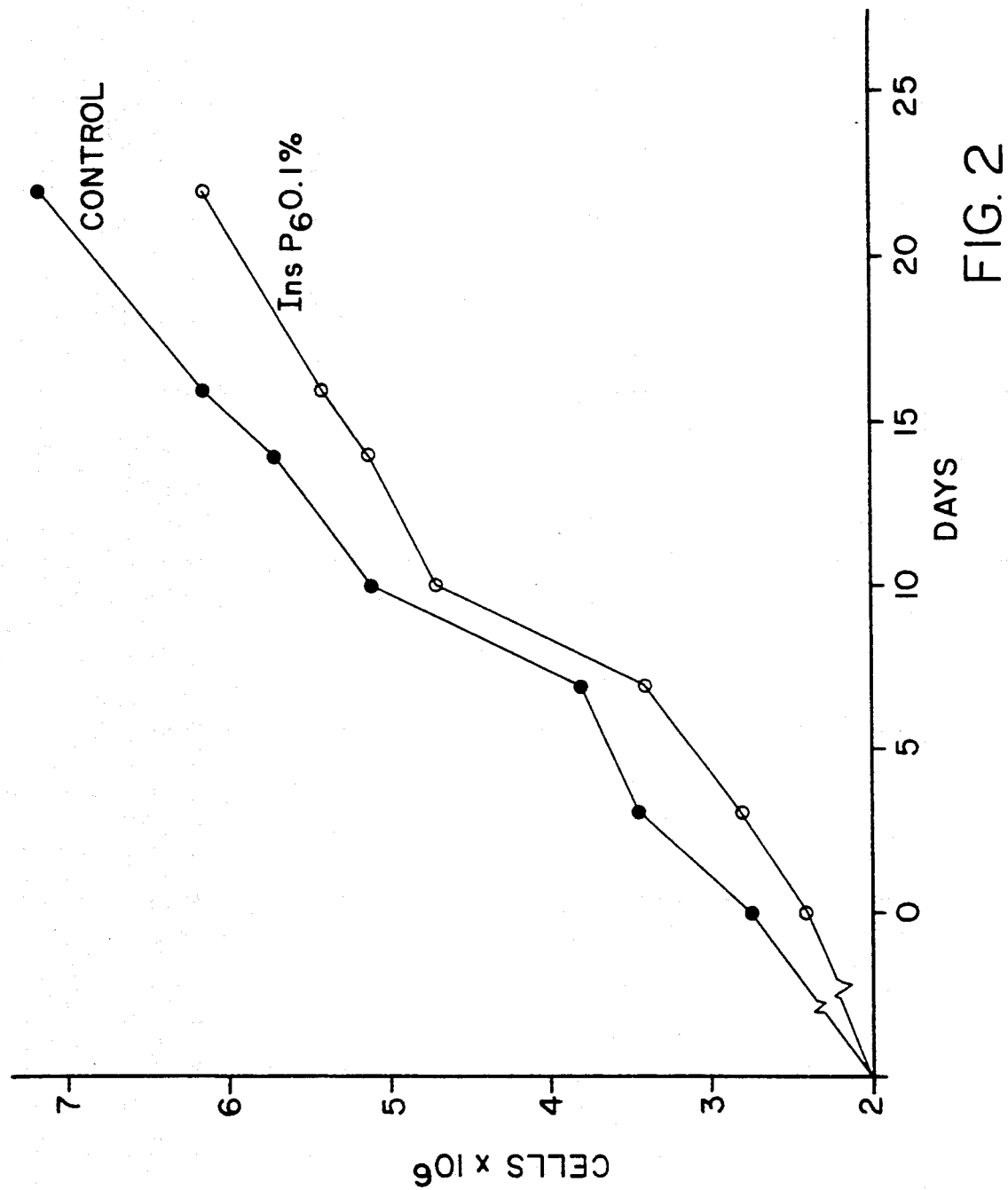
FIG. 2 shows the effect of inositol hexaphosphate on K-562 human leukemia cell line in vitro.
Figure 3:
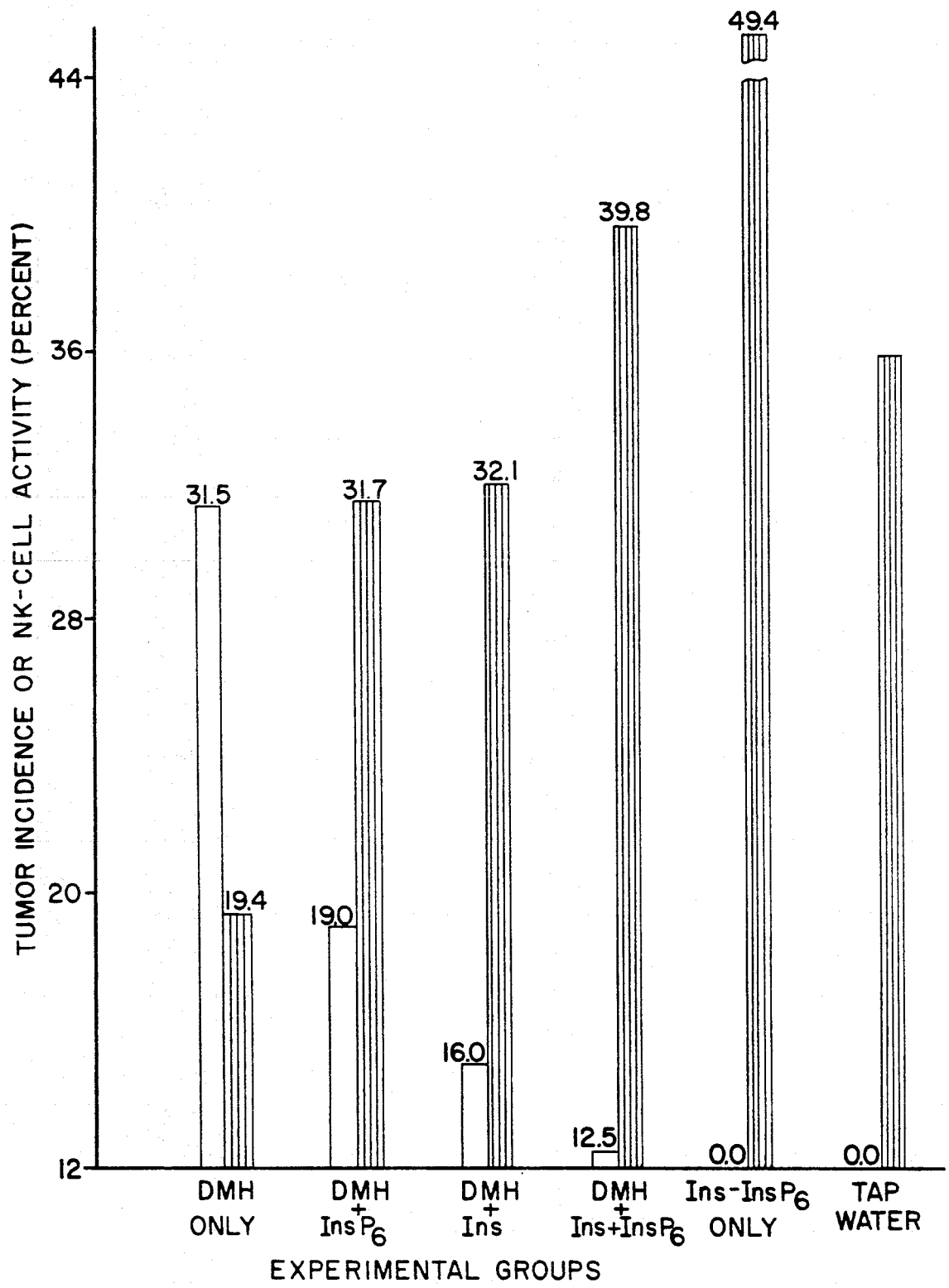
FIG. 3 demonstrates the effect of combined inositol - inositol hexaphosphate treatment on both large intestinal cancer and NK-cell activity in CD-1 mice.
Figure 4:
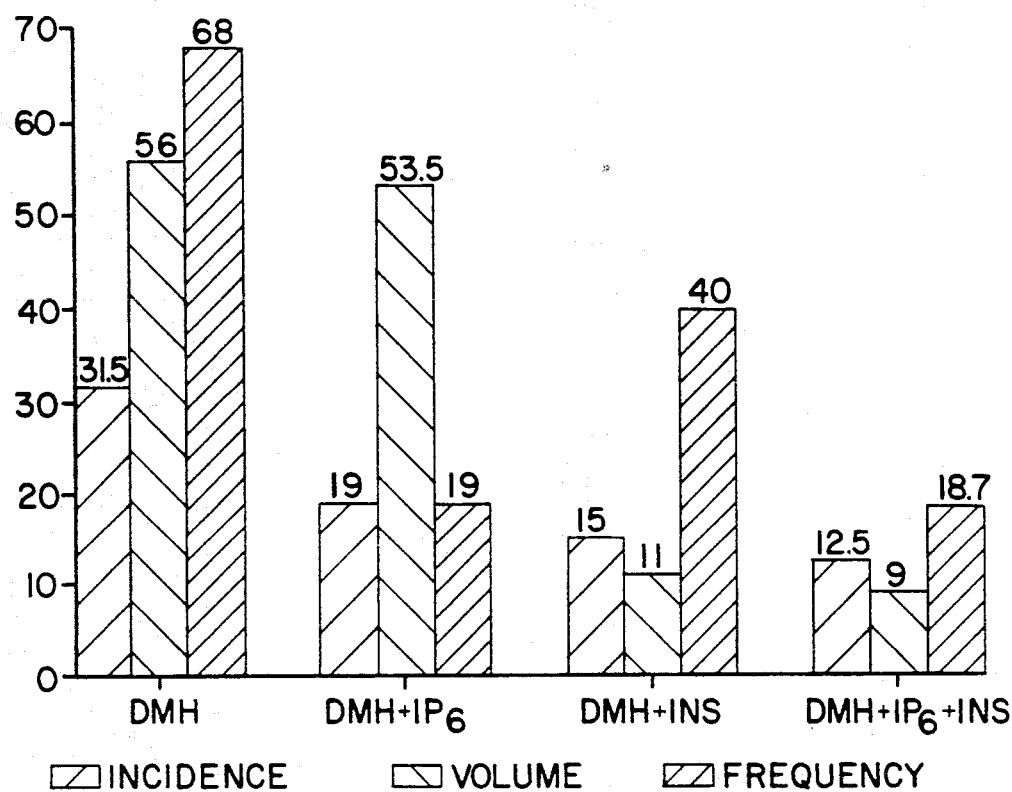
FIGS. 4 and 5 show the relationship between DMH-induced tumor incidence, volume, and frequency with and without administering the composition of this invention.
Figure 5:
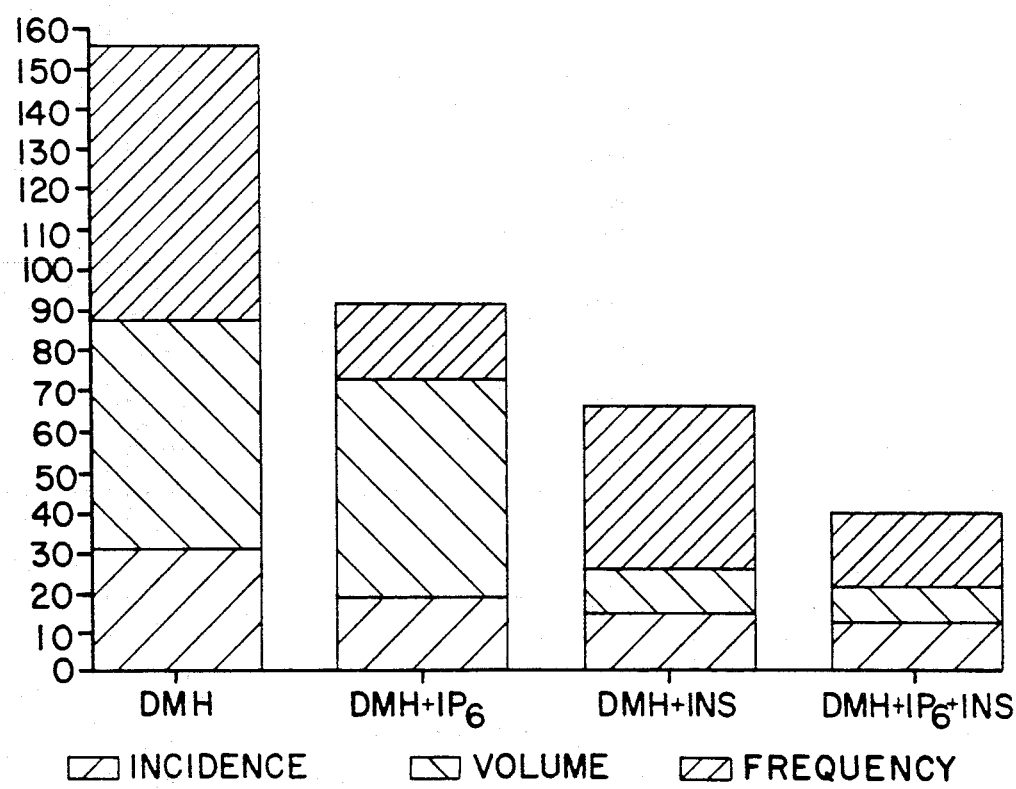

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following Examples, the temperatures are set forth uncorrected in degrees Celsius; unless otherwise indicated, all parts and percentages are by weight.

EXAMPLE 1

Large Intestinal Cancer Inhibition in Rats

Following the procedures of Shamsuddin et al. in *Carcinogenesis* 9(4): 577-580 (1988), F344 rats were treated with the carcinogen azoxymethane (AOM). Ten months after the carcinogen treatment and after five months of $IP_6$ treatment, the results set forth in Table 1 were observed:

TABLE 1

| Group | No. of Tumors in THA | Tumor Volume (cm3) | Tumor Load/Unit area of large intestine |
|---|---|---|---|
| AOM only (n = 16) | 7.13 ± 0.60 | 0.57 ± 0.11 | 0.67 ± 0.07 |
| AOM plus IP (n = 28) | 5.18 ± 0.58 | 0.20 ± 0.06 | 0.38 ± 0.05 |
| Significance | p < 0.02 | p < 0.01 | p < 0.001 |

EXAMPLE 2

Large Intestinal Cancer Inhibition in Mice

Following similarly reported experimental procedures, the pre-induction inhibition of large intestinal cancer by inositol and its hexaphosphate were studied in CD-1 mice, giving the results shown below in Table 2. The only group showing statistically significant reduction in tumor incidence is Group d), with a probability of 0.138 (Fisher) and chi squared $p<0.1$.

TABLE 2

| Treatment Group | Incidence (number of mice with tumors/total) | Frequency (number of tumors per 10 mice) | Tumor Volume (mm$^3$) |
|---|---|---|---|
| a) DMH only | 6/19 (31.6%) | 6.84 | 56 |
| b) DMH + IP$_6$ | 4/21 (19.0%) | 1.90 | 34.5 |
| c) DMH + I | 3/20 (15.0%) | 4.00 | 11 |
| d) DMH + I + IP$_6$ | 2/16 (12.5%) | 1.87 | 9 |
| Control | 0/20 (0.0%) | 0.00 | 0 |

EXAMPLE 3

Cytotoxicity of Murine NK-Cells

Using known procedures, splenic NK cells from control (untreated) mice were either tested directly (control( for cytotoxicity, or were first treated in vitro with 0.05% I plus 0.05% $IP_6$ for one hour at 37° C. Even the short term in vitro treatment greatly enhanced (66% to 94%) NK-cell cytotoxicity at all three tested Effector:Target (E:T) ratios, as shown in Table 3.

TABLE 3

| In Vitro Treatment of NK Cells | E:T 150:1 | E:T 100:1 | E:T 50:1 |
|---|---|---|---|
| No treatment | 31.3 ± 1.2 | 22.6 ± 2.6 | 14.0 ± 1.7 |
| Treatment | 52.0 ± 1.6 | 38.3 ± 1.4 | 27.2 ± 1.8 |
| Significance | p < 0.005 | p < 0.005 | p < 0.005 |

EXAMPLE 4

In vivo Cytotoxicity Tests

Using procedures similar to those of Example 3, the cytotoxicity of murine NK cells were assayed against YAC 1 target cells following in vivo treatment of mice which had been injected subcutaneously with 1,2-dimethylhydrazine (DMH). While either $IP_6$ or I alone had increased the baseline NK activity by approximately 40%, the combination if I - $IP_6$ increased the baseline activity by 57.8%. Likewise, the combination was most effective (~100%) in increasing DMH-induced depressed NK activity. Indeed, it had raised the activity 27% more than the non-DMH treated control animals. The results are summarized in Table 4; values are the means ±SEM of the percent cytotoxicity at an Effector:Target ratio of 150:1.

TABLE 4

| Injection | Supplementation in Diet Drinking Water | | | |
|---|---|---|---|---|
| | none | IP$_6$ | I | I + IP$_6$ |
| saline | 31.3 ± 1.2 | 43.9 ± 2.0 | 44.9 ± 7.4 | 49.4 ± 2.9 |
| DMH | 19.4 ± 1.0 | 31.1 ± 1.9 | 32.1 ± 1.7 | 39.8 ± 1.6 |
| Significance | p < 0.005 | p < 0.005 | p < 0.01 | p < 0.005 |

The preceding examples can be repeated with similar success by substituting the generically or specifically described reactants and/or operating conditions of this invention for those specifically used in the examples. From the foregoing description, one skilled in the art to which this invention pertains can easily ascertain the essential characteristics thereof and, without departing from the spirit and scope of the present invention, can make various changes and modifications to adapt it to various usages and conditions.

INDUSTRIAL APPLICABILITY

As can be seen from the present specification and examples, the present invention is industrially useful in providing a method for moderating the rate of cellular mitosis in a living mammalian tissue having an abnormally high rate of cellular mitosis, sensitive to treatment with a solution of this invention whereby the rate can be reduced to physiologically normal ranges. The present invention is also industrially useful in providing a method for increasing the rate of NK-cell tumoricidal activity in a living mammalian tissue having an abnormally low rate thereof, whereby the rate can be increased to physiologically normal ranges. These two effects frequently but not always occur in combination.

What is claimed is:

1. A method for moderating the rate of cellular mitosis in a living mammal having a pathologically elevated rate of cellular mitosis, which comprises administering to the mammal a safe and effective amount of solution of a) inositol hexaphosphate or a physiologically acceptable salt thereof; and b) inositol or a physiologically acceptable salt thereof, in a molar ratio of a):b) from about 1:3 to 3:1 effective to moderate the elevated rate of cellular mitosis to a normal, non-pathological rate.

2. A method of claim 1, wherein the molar ratio is 1:1.

3. A method according to claim 1, wherein the composition is administered parenterally.

4. A method according to claim 1, wherein the composition is administered orally.

5. A method according to claim 1, wherein the pathological elevated rate of cellular mitosis is caused by cancer or precancer.

6. A method according to claim 5, wherein the cancer is a blood cancer.

7. A method according to claim 5, wherein the cancer is large intestinal cancer.

8. A method for enhancing the rate of KN cell activity in a living mammal having a pathologically or pharmaceutically decreased rate of tumoricidal activity and reduced NK cell activity, which comprises administering to the mammal an amount of a solution of a) inositol hexaphosphate or a physiologically acceptable salt thereof; and b) inositol or a physiologically acceptable salt thereof, in a molar ratio of a):b) of about 1:3 to 3:1, effective to enhance the rate of NK-cell activity to a normal, non-pathological rate.

9. A method according to claim 8, wherein the molar ration is about 1:1.

10. A method according to claim 8, wherein the composition is administered parenterally.

11. A method according to claim 8, wherein the composition is administered orally.

12. A method according to claim 8, wherein the decreased rate of NK-cell activity is caused by immunosuppression.

13. A method according to claim 12, wherein the immunosuppression is caused by an AIDS-related infection.

14. A method according to claim 12, wherein the immunosuppression is pharmaceutically induced by chemotherapy or in preparation for receiving a tissue transplant.

15. A method according to claim 12, wherein the immunosuppression is caused by a bacterial, viral, fungal, or protozoal infection.

16. A pharmaceutical composition capable of a) moderating the rate of cellular mitosis in a living mammal having a pathologically elevated rate of cellular mitosis or b) enhancing the rate of NK cell activity in a living mammal having a pathologically or pharmaceutically decreased rate of tumoricidal activity, which comprises a safe and effective amount and concentration per unit dosage of a composition consisting essentially of a) inositol hexaphosphate or a physiologically acceptable salt thereof; and b) inositol or a physiologically acceptable salt thereof in a molar ratio of a):b) of about 1:3 to 3:1.

17. A composition according to claim 16, wherein the molar ratio of a):b) is about 1:1.

18. A composition according to claim 16, as a sterile liquid adapted for parenteral administration.

19. A composition according to claim 16, as a solid adapted for oral administration.

20. A composition according to claim 16, as a liquid adapted for oral administration.

* * * * *

(12) REEXAMINATION CERTIFICATE (4727th)
United States Patent
Shamsuddin

(10) Number: US 5,082,833 C1
(45) Certificate Issued: Feb. 4, 2003

(54) REDUCTION OF CELL PROLIFERATION AND ENHANCEMENT OF NK-CELL ACTIVITY

(75) Inventor: Abulkalam M. Shamsuddin, 2916 Old Court Rd., Baltimore, MD (US) 21208

(73) Assignee: Abulkalam M. Shamsuddin, Baltimore, MD (US)

Reexamination Request:
No. 90/005,648, Feb. 28, 2000

Reexamination Certificate for:
Patent No.: 5,082,833
Issued: Jan. 21, 1992
Appl. No.: 07/213,889
Filed: Jun. 30, 1988

(51) Int. Cl.[7] ......................... A61K 31/45; A61U 31/66
(52) U.S. Cl. ........................................ 514/143; 514/724
(58) Field of Search ................................. 514/143, 724

(56) References Cited

U.S. PATENT DOCUMENTS 4,952,396 A * 8/1990 Sabin et al. ............... 424/94.6

OTHER PUBLICATIONS

Inositol A Tumor Growth Inhibitor, Laszlo, D. and Leuchtenberger, C, Science 97: 515 (1943).
Chemotherapeutic Regressions of Transplanted and Spontaneous Cancer in Mice, Lewisohn, R., Laszlo, D., Leuchtenberger, C., and Leuchtenberger, R., AAAS, Washington, D. C., pp. 139–207 (1947) (Delivered Aug. 1, 1945, evening session, and Aug. 2, morning session.).
Studies on Tumor Growth–Inhibitory Substances, Daniel Laszlo, AAAS Washington, D.C., pp. 148–156, 1947.
Iron–catalyzed Hydroxyl Radical Formation—Stringent Requirement for Free Iron Coordination Site, Graf, E., Mahoney, J. R., Bryant, R. G. and Eaton, J. W., The Journal of Biological Chemistry, vol. 259, No. 6, Issue of Mar. 25, pp. 3620–3624, 1984.
Applications of Phytic Acid, Graf, E., JAOCS, vol. 60, No. 11 (Nov. 1983), pp. 1861–1867.
"Dietary Suppression of Colonic Cancer—Fiber or Phytate?", Graf, E. and Eaton, J. W., Cancer 56: 717–718, 1985.
Dietary Phytate and Cacium Bioavailability, Graf, E. and Eaton, J. W., Nutritional Bioavailability of calcium, ACS symposium series 275, Washington, D.C.: American Chemical, Society:Apr. 17, 1985: 51–62.
Antioxidant Functions of Phytic Acid, Graf, E. and Eaton, J.W., Free Radical Biology and Medicine, vol. 8, pp. 61–69, 1990.
Fiber and Cancer of the Colon, Irving, D. and Draser, B.S., Br. J. Cancer (1973) 28, 462.
Increasing Use of Soyfoods and Their Potential Role in Cancer Prevention, Messina, M. and Messina, V., Journal of the American Dietetic Association—Perspective In Practice, vol. 91, No. 7, pp. 836–840, Jul. 1991.
Phytate's Potential Role in Reducing Colon–Cancer Risk, Messina, M, American Journal of Clinical Nutrition, pp. 762–763, 1991, Oct. 54 (4).

Effect of Phytic Acid on Colonic Epithelial Cell Proliferation, Nielsen, B.K., Thompson, L.U., and Bird, R.P., Cancer Letters, 37 (1987) 317 325.
Add Some Rice to Your Life, Jariwalla, R.J., Summary of Conference—Disease Prevention by IP6 and other components of Rice, Kyoto, Japan, Jun. 1998. Also published at http://www.tsuno.co.jp/e/u6/m_02.htm.
Post–Initiation Dietary Supplementation with Corn–Derived Inositol Hexaphosphate (IP6) Inhibits Large Intestinal Carcinogenesis in Fisher 344 Rats, Elsayed, A., Ullah, A. and Shamsuddin, A., Federation Proceedings—Federation of American Societies for Experimental Biology. vol. 46, No. 1, Jan. 28, 1987.
Suppression of Large Intestinal Cancer in F 344 Rats by Inositol Hexaphosphate, Shamsuddin, A., Elsayed, A. and Ullah, A., Carcinogenesis vol. 9, No. 4, pp. 577–580, 1988.
Inhibition of Rat Mammary Carcinogenesis by Inositol Hexaphosphate (Phytic Acid). A Pilot Study, Vucenik, I., Shamsuddin, A., Bansal, M. and Kosaku, S., Cancer Letters 75, (1993) 95–102.
The Phytic Acid–Total Phosphorous Relationship in Barley, Oats, Soybeans, and Wheat, Lolas, G., Palamidis, N. and Markakis, P., Ceral Chem. 53:867–871; 1976.
Phytic Acid—A Natural Antioxidant, Graf, E. Empson, K. and Eaton, J.W., J. Biol. Chem. 1987 Aug. 25; 262 (24): 11647–50.
Natural Killer Cells as Antitumor Effector Cells, Herberman, R. and Holden, H, J. Natl. Cancer Inst. 62 (3), 441–445 (1979).
Studies On The Lethal Hit Stage Of Natural Killer Cell–Mediated Cytotoxicity, Graves, S., Bramhall, J. and Bonavida, B., Journal of Immunology, vol. 137, pp. 1977–1984, No. 6. Sep. 15, 1986.

(List continued on next page.)

Primary Examiner—Frederick Krass

(57) ABSTRACT

A method for moderating the rate of cellular mitosis in a living mammalian tissue having a pathologically elevated rate of cellular mitosis sensitive to treatment with a solution below which comprises perfusing said tissue under mitotic growth conditions with a safe and effective amount and concentration of a composition consisting essentially of a) inositol hexaphosphate or a physiologically acceptable salt thereof; and b) a source of inositol or a physiologically acceptable salt thereof, for a period of time sufficient to moderate the elevated rate of cellular mitosis to a normal, non-pathological rate for said tissue. The method is useful in human and mammalian diseases wherein NK cell activity is altered in the laboratory, e.g. tumors, other cancers including leukemia, immunosuppressed individuals (AIDS and transplant receipients), and in viral, fungal or protozoal infections.

OTHER PUBLICATIONS

Natural Killer Cells: Their Role in Deferses Against Disease, Berbeerman, R. and Ortaldo, J., Science 214, 24–30 (1981).

An Index of Tumor Chemotherapy, Dyer, Wilt, Aug. 13, 1951, pp. 10–12, 151 and 152.

Inositol Hexaphosphate from Corn decreased the Frequency of Colorectal Cancer in Azoxymethane–treated Rats, Elsayeo et al, Lab. Invest. vol. 56, MNo. 1, 1987, p. 21 A.

Phytate Concentrations of Leavened and Unleavened Iranian Breads, Reinhold, J. G., Ecology of Food and Nutrition, 1972, vol. 1, pp. 187–192.

myo–Inositiol as an Essential Growth Factor For Normal and Malignant Human Cells in Tissue Culture, Eagle,H., Oyama, V.I., Levy, M. and Freeman, A.E., J. Biol. Chem. 266: 191–205, 1957.

B. Tangendjaja et al., "Analysis of phytic acid by high–performance liquid chromatography", Journal of Chromatography, 197 (1980), pp. 274–277.

* cited by examiner

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–20 is confirmed.

* * * * *